US011017991B2

(12) United States Patent
Goldman

(10) Patent No.: US 11,017,991 B2
(45) Date of Patent: *May 25, 2021

(54) MASS SPECTROMETRIC DETERMINATION OF FATTY ACIDS

(71) Applicant: Quest Diagnostics Investments Incorporated, Wilmington, DE (US)

(72) Inventor: Scott Goldman, Laguna Niguel, CA (US)

(73) Assignee: Quest Diagnostics Investments Incoporated, Wilmington, DE (US)

(*) Notice: Subject to any disclaimer, the term of this patent is extended or adjusted under 35 U.S.C. 154(b) by 40 days.

This patent is subject to a terminal disclaimer.

(21) Appl. No.: 16/359,874

(22) Filed: Mar. 20, 2019

(65) Prior Publication Data

US 2019/0221413 A1 Jul. 18, 2019

Related U.S. Application Data

(63) Continuation of application No. 15/233,322, filed on Aug. 10, 2016, now Pat. No. 10,242,852, which is a continuation of application No. 14/242,075, filed on Apr. 1, 2014, now Pat. No. 9,449,801, which is a continuation of application No. 13/529,844, filed on Jun. 21, 2012, now Pat. No. 8,728,824.

(60) Provisional application No. 61/500,002, filed on Jun. 22, 2011.

(51) Int. Cl.
*H01J 49/00* (2006.01)
*G01N 33/92* (2006.01)
*H01J 49/42* (2006.01)
*H01J 49/10* (2006.01)

(52) U.S. Cl.
CPC .......... *H01J 49/0036* (2013.01); *G01N 33/92* (2013.01); *H01J 49/0027* (2013.01); *H01J 49/10* (2013.01); *H01J 49/426* (2013.01); *G01N 2560/00* (2013.01); *Y10T 436/20* (2015.01); *Y10T 436/200833* (2015.01); *Y10T 436/201666* (2015.01)

(58) Field of Classification Search
CPC ...... H01J 49/0036; H01J 49/00; G01N 33/92; G01N 33/50; G01N 33/48
USPC ....................................................... 436/173
See application file for complete search history.

(56) References Cited

U.S. PATENT DOCUMENTS

| | | | |
|---|---|---|---|
| 5,772,872 A | 6/1998 | Shelhamer |
| 5,795,469 A | 8/1998 | Quinn et al. |
| 5,919,368 A | 7/1999 | Quinn et al. |
| 5,968,367 A | 10/1999 | Quinn et al. |
| 6,107,623 A | 8/2000 | Bateman et al. |
| 6,124,137 A | 9/2000 | Hutchens et al. |
| 6,204,500 B1 | 3/2001 | Whitehouse et al. |
| 6,268,144 B1 | 7/2001 | Koester |
| 8,728,824 B2 | 5/2014 | Goldman |
| 9,449,801 B2 | 9/2016 | Goldman et al. |
| 10,242,852 B2 | 3/2019 | Goldman |
| 2008/0305531 A1 | 12/2008 | Lam et al. |
| 2010/0279956 A1 | 11/2010 | Mc, Jr. et al. |

OTHER PUBLICATIONS

Al-Dirbashi, Rapid UPLC-MS/MS method for routine analysis of plasma pristanic, phytanic, and very long chain fatty acid markers of peroxisomal disorders, Journal of Lipid Reasearch, 2008, vol. 49, p. 1855-1862. (Year: 2008).*
Al-Dirbashi O.Y., et al., "Rapid UPLC-MS/MS Method for Routine Analysis of Plasma Pristanic, Phytanic, and Very Long Chain Fatty Acid Markers of Peroxisomal Disorders," Journal of Lipid Research, 2008, vol. 49 (8), pp. 1855-1862.
Bartolucci G., et al., "Liquid Chromatography Tandem Mass Spectrometric Quantitation of Sulfamethazine and its Metabolites: Direct Analysis of Swine Urine by Triple Quadrupole and by Ion Trap Mass Spectrometry," Rapid communications in Mass Spectrometry, 2000, vol. 14 (11), pp. 967-973.
Butovich I.A., et al., "Cholesteryl Esters as a Depot for Very Long Chain Fatty Acids in Human Meibum," Journal of Lipid Research, 2009, vol. 50 (3), pp. 501-513.
Ferdinandusse S., et al al., "Stereochemistry of the Peroxisomal Branched-chain Fatty Acid a- and Beta-oxidation Systems in Patients Suffering from Different Peroxisomal Disorders," Journal of Lipid Research, 2002, vol. 43 (3), pp. 438-444.
Final Office Action dated Nov. 5, 2015 for U.S. Appl. No. 14/242,075, filed Jan. 4, 2014.
Merchant M., et al., "Recent Advancements in Surface-Enhanced Laser Desorption/Ionization-Time of Flight-Mass Spectrometry," Electrophoresis, 2000, vol. 21 (6), pp. 1164-1167.
Non-Final Office Action dated Jan. 22, 2016 for U.S. Appl. No. 14/063,956, filed Oct. 25, 2013.
Non-Final Office Action dated Aug. 27, 2013 for U.S. Appl. No. 13/529,844, filed Jun. 21, 2012.
Non-Final Office Action dated Mar. 28, 2018 for U.S. Appl. No. 15/233,322, filed Aug. 10, 2016.
Polson C., et al., "Optimization of Protein Precipitation Based Upon Effectiveness of Protein Removal and Ionization Effect in Liquid Chromatography-Tandem Mass Spectrometry," Journal of Chromatography B, 2003, vol. 785 (2), pp. 263-275.
Robb D.B., et al., "Atmospheric Pressure Photoionization: An Ionization Method for Liquid Chromatography-Mass Spectrometry," Analytical Chemistry, 2000, vol. 72 (15), pp. 3653-3659.
Ten-Brink H.J., et al., "Phytanic Acid a-oxidation: Accumulation of 2-hydroxyphytanic Acid and Absence of 2-oxophytanic Acid in Plasma from Patients with Peroxisomal Disorders," Journal of Lipid Research, 1992, vol. 33, pp. 1449-1457.
Ten-Brink H.J., et al., "Pristanic Acid and Phytanic acid in Plasma from Patients with Peroxisomal Disorders: Stable Isotope Dilution Analysis with Electron Capture Negative Ion Mass Fragmentography," Journal of Lipid Research, 1992, vol. 33, pp. 41-47.

(Continued)

*Primary Examiner* — Christine T Mui
(74) *Attorney, Agent, or Firm* — Quest Diagnostics, Inc.

(57) ABSTRACT

The invention relates to the detection of fatty acids. In a particular aspect, the invention relates to methods for detecting very long chain fatty acids and branched chain fatty acids by mass spectrometry.

28 Claims, 15 Drawing Sheets

(56) References Cited

OTHER PUBLICATIONS

Thurman E.M., et al., "LC-MS. I: Basic Principles and Technical Aspects of LC-MS for Pesticide Analysis," Comprehensive Analytical Chemistry XLIII, Femandez A., ed., Elsevier, 2005, Chapter 8, pp. 369-401.
Verhoeven N.M., et al., "Analysis of Pristanic Acid a-oxidation Intermediates in Plasma from Healthy Controls and Patients Affected With Peroxisomal Disorders by Stable Isotope Dilution Gas Chromatography Mass Spectrometry," Journal of Lipid Research, 1999, vol. 40 (2), pp. 260-266.
Verhoeven N.M., et al., "Phytanic Acid and Pristanic Acid are Oxidized by Sequential Peroxisomal and Vlitochondrial Reactions in Cultured Fibroblasts," Journal of Lipid Research, 1998, vol. 39 (1), pp. 66-74.
Wright Jr., G.L., et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures," Prostate Cancer and Prostatic Diseases, 1999, vol. 2 (5-6), pp. 264-276.
Zimmer D., et al., "Comparison of Turbulent-Flow Chromatography with Automated Solid-Phase Extraction in 96-Well Plates and Liquid-Liquid Extraction Used As Plasma Sample Preparation Techniques for Liquid Chromatography-Tandem Mass Spectrometry," Journal of Chromatography A, 1999, vol. 854, pp. 23-35.

\* cited by examiner

MASS SPECTROMETRIC DETERMINATION OF FATTY ACIDS

CROSS REFERENCE TO RELATED APPLICATIONS

This application is a continuation of U.S. application Ser. No. 15/233,322, filed Aug. 10, 2016, now U.S. Pat. No. 10,242,852, which is a continuation of U.S. application Ser. No. 14/242,075, filed Apr. 1, 2014, now U.S. Pat. No. 9,449,801, which is a continuation of U.S. application Ser. No. 13/529,844, filed Jun. 21, 2012, now U.S. Pat. No. 8,728,824, which claims priority to U.S. Provisional Patent Application No. 61/500,002, filed Jun. 22, 2011. The entire contents of the foregoing applications are hereby incorporated by reference in their entirety.

FIELD OF THE INVENTION

The invention relates to the quantitative measurement of fatty acids. In a particular aspect, the invention relates to methods for quantitative measurement of fatty acids by APCI-mass spectrometry.

BACKGROUND OF THE INVENTION

Peroxisomes of eukaryotic cells break down fatty acids that are too long to be oxidized by mitochondria. Two types of fatty acids that are broken down in peroxisomes are very long chain fatty acids (VLCFA) and branched chain fatty acid (BCFA). VLCFA are a family of saturated fatty acids that have branched or unbranched aliphatic tails of 22 carbons or more. Examples of VLCFA with unbranched aliphatic tails include docosanoic acid, tetracosanoic acid, and hexacosanoic acid. Docosanoic acid (also known as behenic acid) is an unbranched saturated fatty acid having a 22 carbon chain. Tetracosanoic acid (also known as lignoceric acid) is an unbranched saturated fatty acid having a 24 carbon chain. Hexacosanoic acid (also known as cerotic acid) is an unbranched saturated fatty acid having a 26 carbon chain. BCFA are saturated or unsaturated fatty acids with aliphatic tails less than 22 carbons long in which other chemical groups, such as methyl groups, extend (i.e., branch) from the aliphatic tail. One example of a BCFA is phytanic acid. Phytanic acid (also known as 3,7,11,15-tetramethyl hexadecanoic acid) is a saturated BCFA 16 carbons long with methyl groups on the $3^{rd}$, $7^{th}$, $11^{th}$, and $15^{th}$ carbons from the carboxylic end of the molecule. Another example of a BCFA is pristanic acid (also known as 2,6,10,14-tetramethylpentadecanoic acid) is a saturated BCFA 15 carbons long with methyl groups on the $2^{nd}$, $6^{th}$, $10^{th}$, and $14^{th}$ carbons from the carboxylic end of the molecule.

Peroxisomes break down VLCFA by β-oxidation. Some BCFA, such as phytanic acid, cannot undergo β-oxidation due to their particular branched structure and are initially broken down in peroxisomes by α-oxidation. For example, phytanic acid is broken down into pristanic acid through α-oxidation, and the pristanic acid is then able to undergo further breakdown via β-oxidation.

Peroxisomal disorders are generally characterized by the inability of peroxisomes to break down VLCFA and BCFA. These disorders include, but are not limited to, Zellweger syndrome, pseudo-Zellweger syndrome, infantile and adult Refsum disease, adrenoleukodystrophy, rhizomelic chondrodysplasia punctata type 1 (RCDP-1), D-bifunctional protein deficiency, and acyl-coA oxidase deficiency. Patients suffering from these types of disorders can accumulate VLCFA and BCFA in their blood and tissue because peroxisomes in these disorders are unable to adequately breakdown VLCFA and BCFA. Thus, it is desirable to be able to detect levels of VLCFA and/or BCFA or their breakdown products in a subject to aid in diagnosis of these disorders.

Quantitation of certain VLCFA by liquid chromatography-mass spectrometry (LC-MS) has been reported. For example, Butovich reports quantitation of derivatized docosanoic acid, tetracosanoic acid, and hexacosanoic acid in meibum by HPLC-APCI (positive ion)-MS (J. Lipid Res. 2009. 50: 501-513); Lam et al. reports quantitation of fatty acids such as oleic acid, linoleic acid, and linolenic acid by LC-ESI (negative ion)-MS from in vitro enzymatic cleavage of plant oils (U.S. Pub. No. 2008/0305531). Al-Dirbashi et al. report quantitation of derivatized VLCFA and BCFA from plasma, using LC-ESI (positive ion)-MS/MS (J. Lipid Res. 2008. 49: 1855-1862).

Other mass spectrometric methods have been reported for quantitation of BCFA. For example, Verhoeven et al. describe using GC-NCI-MS as well as GC-MS/MS to quantitate derivatized BCFA from plasma and cultured fibroblasts, respectively (see J. Lipid Res. 1999. 40:260-266; and J. Lipid Res. 1998. 39:66-74). Fernandusse et al. report using GC-MS to quantitate derivatized BCFA from plasma (J. Lipid Res. 2002. 43: 438-444). In addition, ten Brink et al. report using GC-MS and electron capture NCI to quantitate derivatized BCFA from plasma (see J. Lipid Res. 1992. 33: 1449-1457; and J. Lipid Res. 1992. 33: 41-47).

SUMMARY OF THE INVENTION

The present invention provides methods for detecting the amount of fatty acids in a sample by mass spectrometry.

In one aspect, the invention provides methods for determining the amount of one or more very long chain fatty acids (VLCFA) and/or branched chain fatty acids (BCFA) in a sample by mass spectrometry. In some embodiments, the method comprises the steps of: (a) subjecting one or more VLCFA and/or BCFA from the sample to an atmospheric pressure chemical ionization (APCI) source to generate one or more VLCFA and/or BCFA ions detectable by mass spectrometry; (b) determining the amount of one or more of the VLCFA and/or BCFA ions by mass spectrometry; and (c) relating the amount of the VLCFA and/or BCFA ions to the amount of the VLCFA and/or BCFA in the sample.

In another aspect, the invention provides a method of determining the amount of one or more very long chain fatty acids (VLCFA) and/or branched chain fatty acids (BCFA) in a plasma or serum sample from a human patient comprising: (a) subjecting the sample to a hydrolyzing agent to generate a hydrolyzed sample; (b) purifying the hydrolyzed sample to generate a purified sample; (c) subjecting the purified sample to an atmospheric pressure chemical ionization (APCI) source to generate one or more VLCFA and/or BCFA ions detectable by mass spectrometry; (d) determining the amount of one or more VLCFA and/or BCFA ions by mass spectrometry; and (e) relating the amount of VLCFA and/or BCFA ions determined in step (d) to the amount of the VLCFA and/or BCFA in the sample.

In some embodiments, the amounts of one or more VLCFA are determined. In some of these embodiments, the one or more VLCFA are selected from the group consisting of docosanoic acid, tetracosanoic acid, and hexacosanoic acid. In embodiments where the VLCFA comprises docosanoic acid, the VLCFA ions may comprise ions with a mass to charge ratio (m/z) of 339.3±0.5. In embodiments where the VLCFA comprises tetracosanoic acid, the VLCFA ions may comprise ions with a mass to charge ratio (m/z) of 367.3±0.5. In embodiments where the VLCFA comprises hexacosanoic acid, the VLCFA ions may comprise ions with a mass to charge ratio (m/z) of 395.4±0.5.

In some embodiments, the amounts of one or more BCFA are determined. In some of these embodiments, the BCFA are methyl-BCFA, such as a BCFA selected from the group consisting of pristanic acid and phytanic acid. In embodiments where the BCFA comprises pristanic acid, the BCFA ions may comprise ions with a mass to charge ratio (m/z) of 297.3±0.5. In embodiments where the BCFA comprises phytanic acid, the BCFA ions may comprise ions with a mass to charge ratio (m/z) of 311.2±0.5.

In some embodiments, the APCI source is operating in negative ionization mode. In some embodiments, the amounts of one or more VLCFA and one or more BCFA are determined. In some embodiments, the VLCFA are selected from the group consisting of docosanoic acid, tetracosanoic acid, and hexacosanoic acid. In some embodiments, the BCFA are selected from the group consisting of pristanic acid and phytanic acid. In some embodiments, the fatty acid analytes are underivatized prior to ionization. In some embodiments, the sample comprises a biological sample, such as a sample derived from a human, such as plasma or serum. In some embodiments, the sample is subjected to a hydrolyzing agent prior to ionization. In some embodiments, the hydrolyzing agent is an acid or a base. In some embodiments, the sample is subjected to liquid/liquid extraction prior to ionization. In some embodiments, the VLCFA and/or BCFA are subjected to a liquid chromatography column prior to ionization. In some embodiments, the liquid chromatography column comprises a high performance liquid chromatography (HPLC) column.

In some embodiments, the human patient is suspected of having a peroxisomal disorder, such as Zellweger syndrome, pseudo-Zellweger syndrome, infantile and adult Refsum disease, adrenoleukodystrophy, rhizomelic chondrodysplasia punctata type 1 (RCDP-1), D-bifunctional protein deficiency, and acyl-coA oxidase deficiency. In some embodiments, VLCFA and/or BCFA are quantitated in a patient sample to diagnose, prognose, or monitor the treatment of a patient with a peroxisomal disorder.

As used herein, "very long chain fatty acids" (or "VLCFA") are fatty acids with aliphatic tails of 22 carbons or longer in length. The aliphatic tails of VLCFA may be branched or unbranched, and saturated or unsaturated. In certain embodiments, the methods described herein may be used to determine the amount of one or more unbranched saturated VLCFA in a sample. Examples of unbranched, saturated VLCFA include docosanoic acid, tetracosanoic acid, hexacosanoic acid.

As used herein, "branched chain fatty acids" (or "BCFA") are fatty acids with aliphatic tails less than 22 carbons long that have side chains (or "branches"). Typically, the side chains are methyl groups, and the side chains may occur at one or more locations along the aliphatic tail. In certain embodiments, the methods described herein are used to determine the amount of one or more methyl-branched chain fatty acids (methyl-BCFA) in a sample. Examples of methyl-BCFA include pristanic acid and phytanic acid.

As used herein, "derivatizing" means reacting two or more molecules to form a new molecule. As used herein, the names of derivatized forms of compounds (including fatty acids such as phytanic acid and docosanoic acid) include an indication as to the nature of derivatization. For example, the methyl esters of phytanic acid and docosanoic acid would be referred to as phytanic acid-methyl ester and docosanoic acid-methyl ester.

Mass spectrometry may be performed in negative ion mode. Alternatively, mass spectrometry may be performed in positive ion mode. Various ionization sources, including for example atmospheric pressure chemical ionization (APCI), laser diode thermal desorption (LDTD), or electrospray ionization (ESI), may be used in embodiments of the present invention. In certain preferred embodiments, VLCFA and/or BCFA are measured using APCI in negative ion mode.

In preferred embodiments, one or more separately detectable internal standards are provided in the sample, the amount of which are also determined in the sample. In these embodiments, all or a portion of both the analyte(s) of interest and the internal standard(s) present in the sample are ionized to produce a plurality of ions detectable in a mass spectrometer, and one or more ions produced from each analyte of interest and internal standard are detected by mass spectrometry. Exemplary internal standards for fatty acids include pristanic acid-$^2H_3$, phytanic acid-$^2H_3$, docosanoic acid-$^2H_3$, tetracosanoic acid-$^2H_3$, and hexacosanoic acid-$^2H_3$.

Ions detectable in a mass spectrometer may be generated for each of the exemplary internal standards listed above. Exemplary spectra generated demonstrating detection of pristanic acid-$^2H_3$, phytanic acid-$^2H_3$, docosanoic acid-$^2H_3$, tetracosanoic acid-$^2H_3$, and hexacosanoic acid-$^2H_3$ are discussed in Example 4, and shown in FIGS. 6-10, respectively.

As used herein, an "isotopic label" produces a mass shift in the labeled molecule relative to the unlabeled molecule when analyzed by mass spectrometric techniques. Examples of suitable labels include deuterium (d or $^2H$), $^{13}C$, and $^{15}N$. For example, phytanic acid-$^2H_3$ and docosanoic acid-$^2H_3$ have masses of about 3 mass units higher than unlabeled phytanic acid and docosanoic acid. The isotopic label can be incorporated at one or more positions in the molecule and one or more kinds of isotopic labels can be used on the same isotopically labeled molecule.

In other embodiments, amounts of VLCFA and/or BCFA ions may be determined by comparison to one or more external reference standards. Exemplary external reference standards include blank plasma or serum spiked with one or more of pristanic acid-$^2H_3$, phytanic acid-$^2H_3$, docosanoic acid-$^2H_3$, tetracosanoic acid-$^2H_3$, and hexacosanoic acid-$^2H_3$. External standards typically will undergo the same treatment and analysis as any other sample to be analyzed.

As used herein, unless otherwise stated, the singular forms "a," "an," and "the" include plural reference. Thus, for example, a reference to "a protein" includes a plurality of protein molecules.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE, including TFLC, may operate via a unitary or mixed mode mechanism. Mixed mode mechanisms utilize ion exchange and hydrophobic retention in the same column; for example, the solid phase of a mixed-mode SPE column may exhibit strong anion exchange and hydrophobic retention; or may exhibit strong cation exchange and hydrophobic retention.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr. A* 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 µm.

As used herein, the term "analytical column" refers to a chromatography column having sufficient chromatographic plates to effect a separation of materials in a sample that elute from the column sufficient to allow a determination of the presence or amount of an analyte. In a preferred embodiment, the analytical column contains particles of about 5 µm in diameter. Such columns are often distinguished from "extraction columns", which have the general purpose of separating or extracting retained material from non-retained materials in order to obtain a purified sample for further analysis.

As used herein, the terms "on-line" and "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged species; and (2) detecting the charged species based on their mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21: 1164-67.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to a form of ionization where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., *Anal. Chem.* 2000, 72 (15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "desorption" refers to the removal of an analyte from a surface and/or the entry of an analyte into a gaseous phase. Laser diode thermal desorption (LDTD) is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample may then be drawn into an ionization source, where the gas phase sample is ionized in preparation for analysis in the mass spectrometer. When using LDTD, ionization of the gas phase sample may be accomplished by any suitable technique known in the art, such as by ionization with a corona discharge (for example by APCI).

As used herein, the term "field desorption" refers to methods in which a non-volatile test sample is placed on an ionization surface, and an intense electric field is used to generate analyte ions.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "lower limit of quantification", "lower limit of quantitation" or "LLOQ" refers to the point where measurements become quantitatively meaningful. The analyte response at this LLOQ is identifiable, discrete and reproducible with a concentration at which the standard deviation (SD) is less than one third of the total allowable error (TEa).

As used herein, the term "limit of detection" or "LOD" is the point at which the measured value is larger than the uncertainty associated with it. The LOD is the point at which a value is beyond the uncertainty associated with its measurement and is defined as the mean of the blank plus four times the standard deviation of the blank.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

BRIEF DESCRIPTION OF THE DRAWINGS

FIG. 1B). Details are discussed in Example 4.

FIG. 2B). Details are discussed in Example 4.

FIG. 3B). Details are discussed in Example 4.

FIG. 4B). Details are discussed in Example 4.

FIG. 5B). Details are discussed in Example 4.

DETAILED DESCRIPTION OF THE INVENTION

Figure 1A:
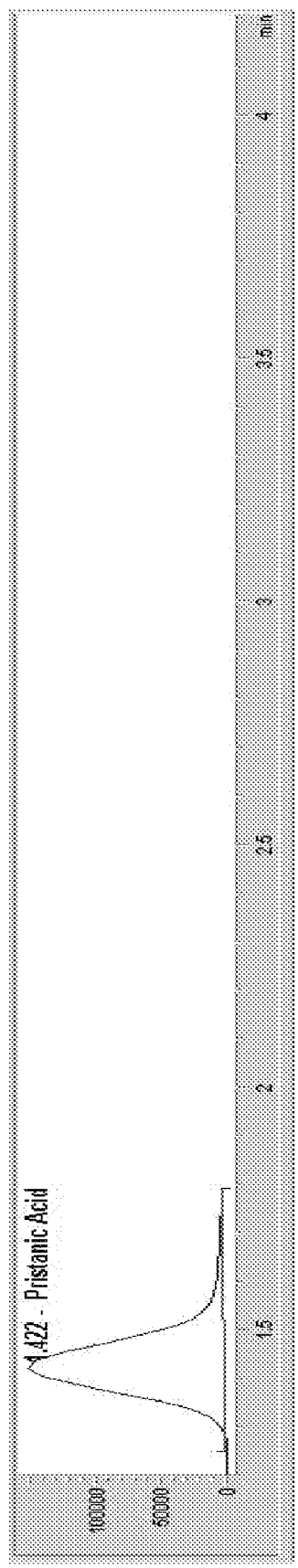
FIGS. 1A and 1B show exemplary chromatograms for pristanic acid (FIG. 1A) and pristanic acid-$^2H_3$ (internal standard.
Figure 1B:
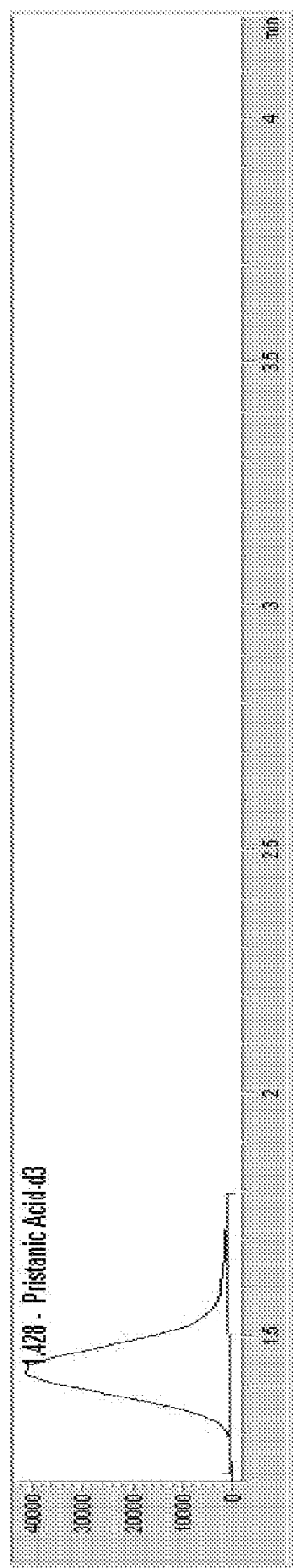
Figure 2A:
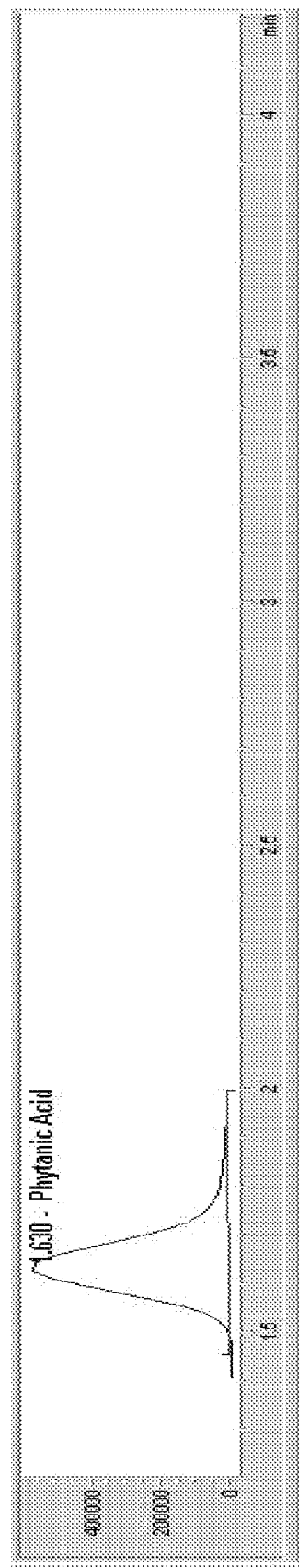
FIGS. 2A and 2B show exemplary chromatograms for phytanic acid (FIG. 2A) and phytanic acid-$^2H_3$ (internal standard.
Figure 2B:
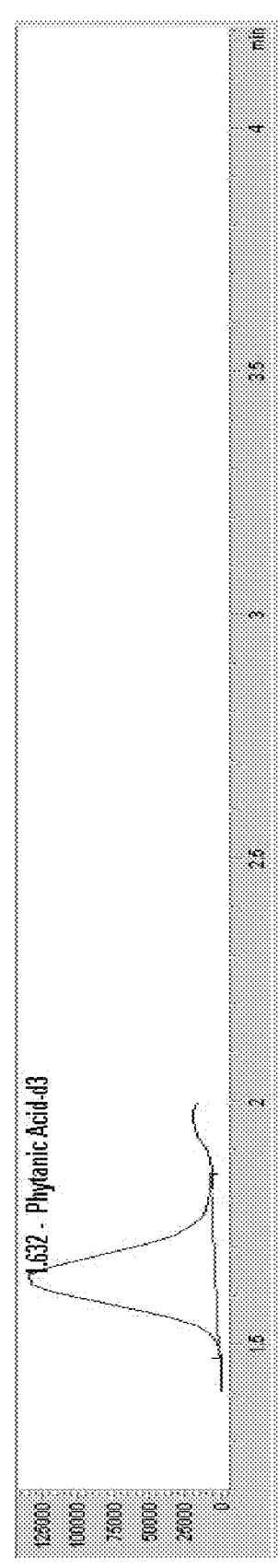
Figure 3A:
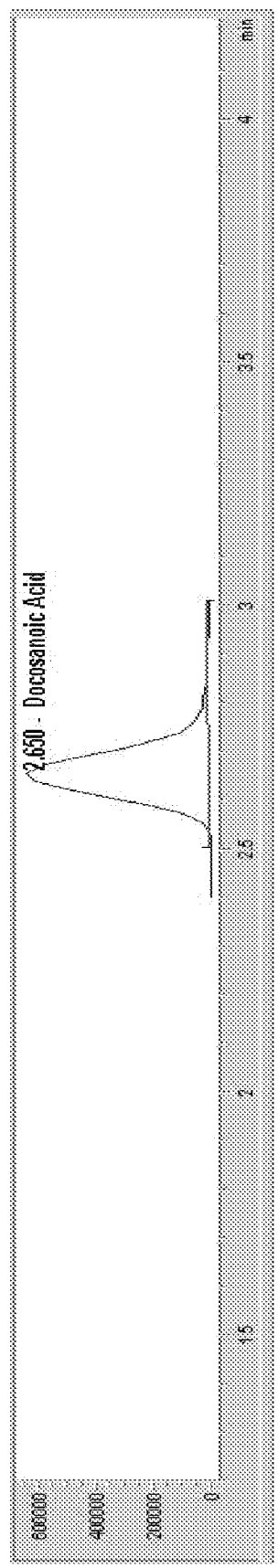
FIGS. 3A and 3B show exemplary chromatograms for docosanoic acid (FIG. 3A) and docosanoic acid-$^2H_3$ (internal standard.
Figure 3B:
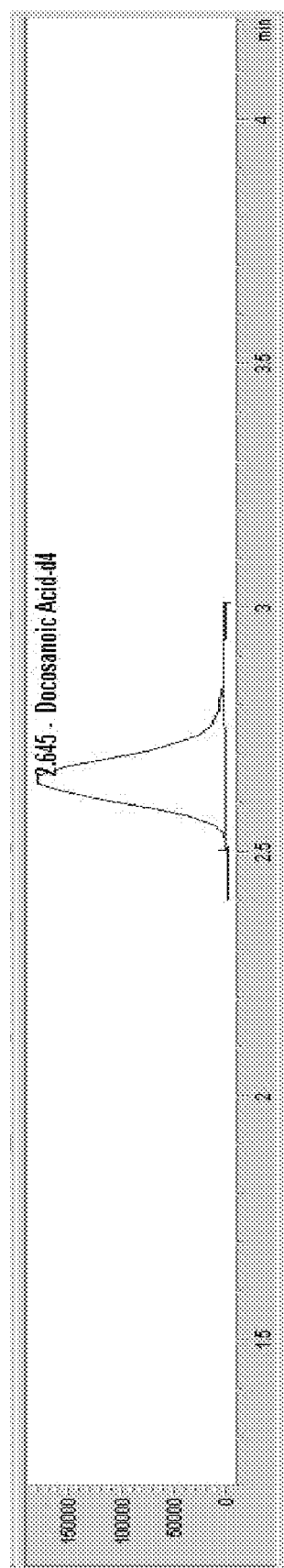
Figure 4A:
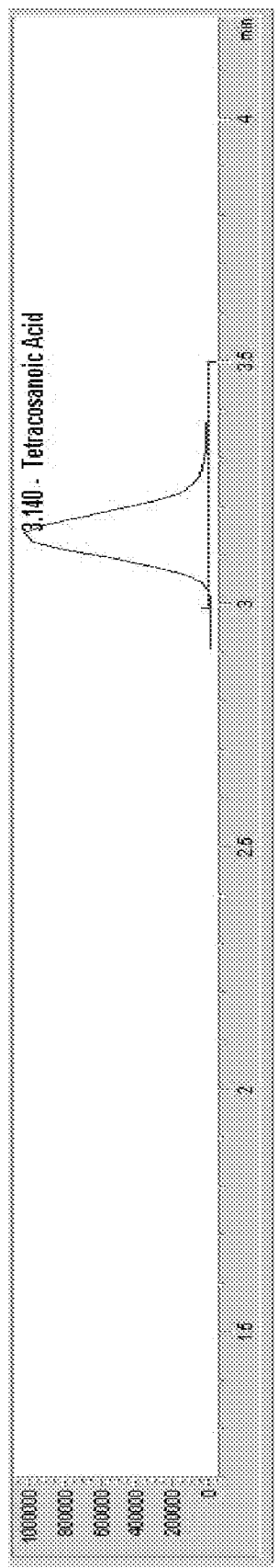
FIGS. 4A and 4B show exemplary chromatograms for tetracosanoic acid (FIG. 4A) and tetracosanoic acid-$^2H_3$ (internal standard.
Figure 4B:
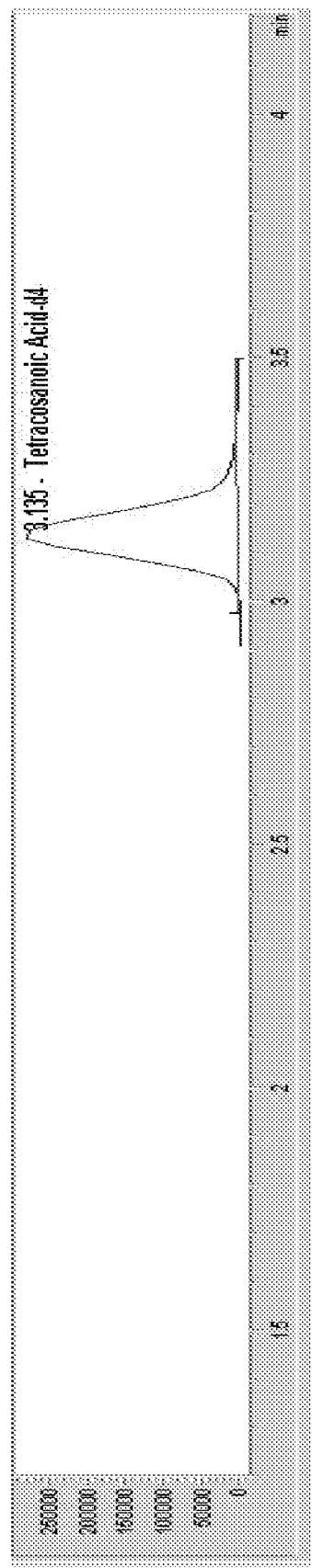
Figure 5A:
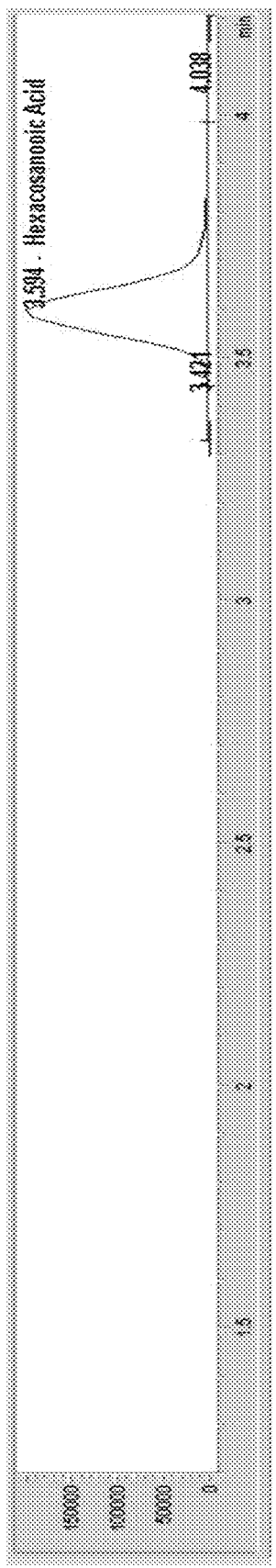
FIGS. 5A and 5B show exemplary chromatograms for hexacosanoic acid (FIG. 5A) and hexacosanoic acid-$^2H_3$ (internal standard.
Figure 5B:
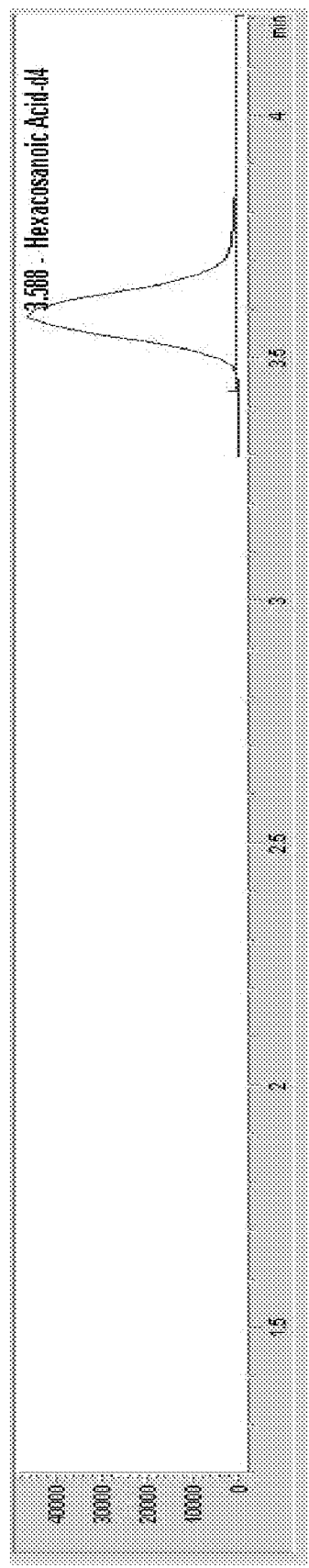

Methods are described for measuring fatty acids in a sample. More specifically, mass spectrometric methods are described for detecting and quantifying fatty acids in a sample. The methods may utilize APCI to ionize underivatized VLCFA and/or BCFA in the sample prior to detection by mass spectrometry.

The methods may use an on-line analytical liquid chromatography technique, such as high performance liquid chromatography (HPLC), to perform a purification of VLCFA and/or BCFA, combined with methods of mass spectrometry (MS), thereby providing a high-throughput assay system for detecting and quantifying fatty acids in a sample. Preferred embodiments are particularly well suited for application in large clinical laboratories for automated VLCFA and/or BCFA quantitation.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as blood, plasma, serum, saliva, cerebrospinal fluid, or tissue samples; preferably plasma (including EDTA and heparin plasma) and serum. Such samples may be obtained, for example, from a patient; that is, a living person, male or female, presenting oneself in a clinical setting for diagnosis, prognosis, or treatment of a disease or condition.

The present invention also contemplates kits for a VLCFA and/or BCFA quantitation assay. A kit for a VLCFA and/or BCFA quantitation assay may include a kit comprising the compositions provided herein. For example, a kit may include packaging material and measured amounts of packaged reagents, including an isotopically labeled internal standard, in amounts sufficient for at least one assay. Typically, the kits will also include instructions recorded in a tangible form (e.g., contained on paper or an electronic medium) for using the packaged reagents for use in a VLCFA and/or BCFA quantitation assay.

Calibration and QC pools for use in embodiments of the present invention are preferably prepared using a matrix similar to the intended sample matrix.

Sample Preparation for Mass Spectrometric Analysis

In preparation for mass spectrometric analysis, VLCFA and/or BCFA (including pristanic acid, phytanic acid, docosanoic acid, tetracosanoic acid, and/or hexacosanoic acid) in the sample may be enriched relative to their ester counterparts by hydrolysis of fatty acid esters by any technique known in the art. In some embodiments, fatty acid esters in the sample are hydrolyzed by contacting the sample with a strong acid (e.g., HCl) or a strong base (e.g., NaOH) and optionally incubating at an elevated temperature, such as about 120° C. to about 125° C. The incubation period may vary depending on the amount of sample and concentration of acid used. Certain embodiments described herein utilize an incubation period of about 60 minutes to hydrolyze 200 µL of sample, diluted with 100 µL of internal standard, with 200 µL of 1 M NaOH. After incubation, excess hydroxide may be neutralized by treatment with an acid, such as hydrochloric acid (HCl).

Additionally, VLCFA and/or BCFA may be enriched relative to one or more other components in the sample (e.g. protein) by various methods known in the art, including for example any combination of liquid chromatography, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like. If both hydrolysis and purification steps are used, purification is preferably conducted after hydrolysis.

Protein precipitation is one method of preparing a test sample, especially a biological test sample, such as serum or plasma. Protein purification methods are well known in the art, for example, Polson et al., *Journal of Chromatography B* 2003, 785:263-275, describes protein precipitation techniques suitable for use in methods of the present invention. Protein precipitation may be used to remove most of the protein from the sample leaving fatty acids in the supernatant. The samples may be centrifuged to separate the liquid supernatant from the precipitated proteins; alternatively the samples may be filtered to remove precipitated proteins. The resultant supernatant or filtrate may then be applied directly to mass spectrometry analysis; or alternatively to liquid chromatography and subsequent mass spectrometry analysis. In certain embodiments, samples, such as plasma or serum, may be purified by a hybrid protein precipitation/liquid-liquid extraction method. In these embodiments, a sample is mixed with methanol, ethyl acetate, and water, and the resulting mixture is vortexed and centrifuged. The resulting supernatant is removed, dried to completion and reconstituted in a suitable solvent. In certain embodiments described herein, the solvent used to reconstitute the dried supernatant is ethanol.

Another method of sample purification that may be used prior to mass spectrometry is liquid chromatography (LC). Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a diffusional process and may select LC, including HPLC, instruments and columns that are suitable for use with fatty acids. The chromatographic column typically includes a medium (i.e., a packing material) to facilitate separation of chemical moieties (i.e., fractionation). The medium may include minute particles, or may include a monolithic material with porous channels. A surface of the medium typically includes a bonded surface that interacts with the various chemical moieties to facilitate separation of the chemical moieties. One suitable bonded surface is a hydrophobic bonded surface such as an alkyl bonded, cyano bonded surface, or highly pure silica surface. Alkyl bonded surfaces may include C-4, C-8, C-12, or C-18 bonded alkyl groups. In preferred embodiments, the column is a C-18 alkyl bonded column (such as a BDS HYPERSIL™ (C18 alkyl chain) column from Thermo Scientific). The chromatographic column includes an inlet port for receiving a sample and an outlet port for discharging an effluent that includes the fractionated sample. The sample may be supplied to the inlet port directly, or from an extraction column, such as an on-line SPE cartridge or a TFLC extraction column.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytypic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition may be employed where the analyte of interest is retained by the column, and a second mobile phase condition may subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, HPLC is conducted with an alkyl bonded analytical column chromatographic system. In certain preferred embodiments, a C-18 alkyl bonded column (such as a BDS HYPERSIL™ (C18 alkyl chain) column from Thermo Scientific) is used. In certain embodiments, HPLC is performed using 20 mM ammonium acetate as mobile phase A and 100% acetonitrile as mobile phase B.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, an extraction column may be used for purification of VLCFA and/or BCFA prior to mass spectrometry. In such embodiments, samples may be extracted using an extraction column which captures the analyte, then eluted and chromatographed on a second extraction column or on an analytical HPLC column prior to ionization. For example, sample extraction with a TFLC extraction column may be accomplished with a large particle size (e.g. greater than 50 µm) packed column. Sample eluted off of this column may then be transferred to an HPLC analytical column for further purification prior to mass spectrometry. Because the steps involved in these chromatography procedures may be linked in an automated fashion, the requirement for operator involvement during the purification of the analyte can be minimized. This feature may result in savings of time and costs, and eliminate the opportunity for operator error.

In some embodiments, purification of VLCFA and/or BCFA is accomplished with liquid-liquid extraction. Liquid/liquid extraction may be accomplished by adding a suitable quantity of an organic solvent, such as 10% ethyl acetate in hexane, to the sample. This mixture is then agitated, such as by vortexing, and chilled, and the organic layer is decanted off for further analysis. In some embodiments, VLCFA and/or BCFA in the sample may be purified by liquid/liquid extraction followed by liquid chromatography prior to mass spectrometric analysis.

Detection and Quantitation by Mass Spectrometry

Mass spectrometry is performed using a mass spectrometer, which includes an ionization source for ionizing the fractionated sample and creating charged molecules for further analysis. For example, ionization of the sample may be performed by electron ionization, chemical ionization, electrospray ionization (ESI), photon ionization, atmospheric pressure chemical ionization (APCI), photoionization, atmospheric pressure photoionization (APPI), laser diode thermal desorption (LDTD), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. In preferred embodiments, VLCFA and/or BCFA in the sample are ionized by APCI.

Mass spectrometric techniques may be conducted in positive or negative ionization mode. In preferred embodiments, VLCFA and/or BCFA are ionized in negative ionization mode.

In mass spectrometry techniques generally, after the sample has been ionized, the positively or negatively charged ions created thereby may be analyzed to determine a mass-to-charge ratio. Suitable analyzers for determining mass-to-charge ratios include quadrupole analyzers, ion traps analyzers, and time-of-flight analyzers. Exemplary ion trap methods are described in Bartolucci, et al., *Rapid Commun. Mass Spectrom.* 2000, 14:967-73.

Ions in a MS system may be detected using several detection modes. For example, selected ions may be detected, i.e. using a selective ion monitoring mode (SIM), or alternatively, mass transitions resulting from collision induced dissociation or neutral loss may be monitored, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

Alternate modes of operating a tandem mass spectrometric instrument include product ion scanning and precursor ion scanning. For a description of these modes of operation, see, e.g., E. Michael Thurman, et al., *Chromatographic-Mass Spectrometric Food Analysis for Trace Determination of Pesticide Residues*, Chapter 8 (Amadeo R. Fernandez-Alba, ed., Elsevier 2005) (387).

The results of an analyte assay may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, external standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of VLCFA and/or BCFA in the sample. Methods of generating and using such standard curves are well known in the art and one of ordinary skill is capable of selecting an appropriate internal standard. For example, in some embodiments one or more isotopically labeled fatty acids (e.g., pristanic acid-$^2H_3$, phytanic acid-$^2H_3$, docosanoic acid-$^2H_3$, tetracosanoic acid-$^2H_3$, hexadocosanoic acid-$^2H_3$) may be used as internal standards. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the purification and mass spectrometry steps may be performed in an on-line fashion.

In certain embodiments, such as MS/MS, where precursor ions are isolated for further fragmentation, collision activated dissociation (CAD) is often used to generate fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In some preferred embodiments, fatty acids in a sample are detected and/or quantitated using MS as follows. The samples are first purified by liquid-liquid extraction. Then, the purified sample is subjected to liquid chromatography, preferably on an analytical column (such as a HPLC column) and the flow of eluted fatty acids from the chromatographic column is directed to the ionization source of an MS analyzer. Fatty acids from the chromatographic column are ionized via APCI in negative ionization mode. The generated ions pass through the orifice of the instrument and enter a series of three quadrupoles (Q1, Q2, and Q3). Q1 acts as a mass filter, allowing selection of ions (i.e., selection of "precursor" ions) to pass into Q2 based on their mass to charge ratio (m/z). Q2 acts as a collision chamber where precursor ions are fragmented into fragment ions. Q3 acts as a mass filter allowing for selection of ions (i.e. fragment ions) based on their m/z. The three quadrupoles select for ions with the mass to charge ratios of fatty acids ions of interest. Ions with the correct mass/charge ratios are allowed to pass the quadrupoles and collide with the detector.

As ions collide with the detector they produce a pulse of electrons that are converted to a digital signal. The acquired data is relayed to a computer, which plots counts of the ions collected versus time. The areas under the peaks corresponding to particular ions, or the amplitude of such peaks, may be measured and correlated to the amount of the analyte of interest. In certain embodiments, the area under the curves, or amplitude of the peaks, for VLCFA and/or BCFA ions are measured to determine the amount of VLCFA and/or BCFA in the original sample. As described above, the relative abundance of a given ion may be converted into an absolute amount of the original analyte using calibration standard curves based on peaks of one or more ions of an internal molecular standard.

The following Examples serve to illustrate the invention. These Examples are in no way intended to limit the scope of the methods. In particular, the Examples demonstrate quantitation of very long chain fatty acids (VLCFA) and branched chain fatty acids (BCFA) by mass spectrometry, and the use of VLCFA-$^2$H$_3$ and BCFA-$^2$H$_3$ as internal standards. The use of VLCFA-$^2$H$_3$ and BCFA-$^2$H$_3$ as internal standards are not meant to be limiting in any way. Any appropriate chemical species, easily determined by one in the art, may be used as an internal standard.

EXAMPLES

Example 1: Hydrolysis of Fatty Acid Esters and Liquid-Liquid Extraction

The following hydrolysis and liquid-liquid extraction techniques were conducted on controls, standards, and patient serum samples to prepare samples for mass spectrometric analysis. Plasma samples were also tested with similar results (not shown).

First, 100 µL of an isotopically labeled VLCFA-$^2$H$_3$ and/or BCFA-$^2$H$_3$ internal standard mixture was mixed with 200 µL aliquots of each standard, control, and patient sample. 200 µL of 1.0M NaOH were added to the sample mixture and the NaOH-treated mixture was heated at temperatures between about 120° C. and 125° C. for about 60 minutes. The mixtures were then removed and allowed to cool for about 5 minutes.

After cooling, 400 µL of 5M HCl was added to each cooled sample mixture and vortexed briefly. The sample mixture was then re-heated at temperatures between about 120° C. and 125° C. for about 75 minutes. After incubation was complete, the mixtures were again allowed to cool for about 5 minutes.

3.5 mL of 10% ethyl acetate in hexane was then added to each sample; the resulting mixtures vortexed for 3 minutes and centrifuged at 2500 rpm for 5 minutes. After centrifugation, the samples were placed in a methanol/dry ice bath for 5 minutes to freeze the aqueous later. The organic layer was then decanted off, dried to completion under a flowing nitrogen gas manifold, and reconstituted in 150 µL of ethanol.

The resulting samples were transferred to HPLC vials and placed in an autosampler for analysis.

Example 2: Purification of VLCFA and/or BCFA with Liquid Chromatography

Sample injection was performed with an Agilent Technologies G1367B Autosampler.

The autosampler system automatically injected an aliquot of the above prepared reconstituted samples into a Thermo Scientific BDS HYPERSIL™ (C18 alkyl chain) HPLC column (3 µm particle size, 100×2.1 mm, from Thermo Scientific). An HPLC gradient was applied to the analytical column, to separate VLCFA and BCFA from other components in the sample. Mobile phase A was 20 mM ammonium acetate and mobile phase B was 82% acetonitrile in methanol. The HPLC gradient started with an 82% solvent B which was ramped to 90% in approximately 1 minute, then ramped up to 95% for another minute, and held at that percentage for approximately 36 seconds, before being ramped back down to 90% over the next one minute and 18 seconds, and then down to 82% over the next 24 seconds. Column flow rate during solvent application was about 0.85 mL/min. Pristanic acid, phytanic acid, docosanoic acid, tetracosanoic acid, and hexacosanoic acid were observed to elute off the column at approximately 1.43 minutes into the gradient profile.

Example 4: Detection and Quantitation of VLCFA and/or BCFA by MS

MS was performed on the above eluted samples using an Agilent 6130 Single Quadrupole Mass Spectrometer. Liquid solvent/analyte exiting the analytical column flowed to the ionization interface of the MS/MS analyzer. The solvent/analyte mixture was converted to vapor in the tubing of the interface. Analytes in the nebulized solvent were ionized by APCI.

Ions passed to the quadrupole mass selector (Q1), which selected pristanic acid, phytanic acid, docosanoic acid, tetracosanoic acid, and hexacosanoic acid ions with mass-to-charge ratios (m/z) of 297.3±0.5, 311.2±0.5, 339.3±0.5, 367.3±0.5, and 395.4±0.5, respectively. The selected ions then traveled to a detector for counting. Mass spectrometer settings used for this Example are shown in Table 1. Simultaneously, the same process using isotope dilution mass spectrometry was carried out with internal standards: pristanic acid-$^2$H$_3$, phytanic acid-$^2$H$_3$, docosanoic acid-$^2$H$_3$, tetracosanoic acid-$^2$H$_3$, and hexacosanoic acid-$^2$H$_3$. The masses monitored for detection and quantitation during validation on negative polarity are shown in Table 2.

TABLE 1

Mass Spectrometer Settings for Detection of Very Long Chain Fatty Acids and Internal Standards (Negative Ionization)
Mass Spectrometric Instrument Settings

| | |
|---|---|
| Gas Temperature | 350° C. |
| Vaporizer Temperature | 245° C. |
| Drying Gas Flow | 12.0 L/min |
| Nebulizer Pressure | 50 psig |
| Vcap (positive) | 4000 V |
| Vcap (negative) | 1800 V |
| Vcharge (positive) | 2000 V |
| Vcharge (negative) | 1000 V |
| Corona (positive) | 5.0 µA |
| Corona (negative) | 40 µA |

TABLE 2

Mass-to-Charge ratios monitored for Very Long Chain Fatty Acids and Internal Standards (Negative Ionization)

| Analyte | Ion (m/z) |
|---|---|
| Pristanic acid | 297.3 ± 0.5 |
| Phytanic acid | 311.2 ± 0.5 |
| Docosanoic acid | 339.3 ± 0.5 |

TABLE 2-continued

Mass-to-Charge ratios monitored for Very Long Chain Fatty Acids and Internal Standards (Negative Ionization)

| Analyte | Ion (m/z) |
|---|---|
| Tetracosanoic acid | 367.3 ± 0.5 |
| Hexadocosanoic acid | 395.4 ± 0.5 |
| Pristanic acid-$^2$H$_3$ | 300.3 ± 0.5 |
| Phytanic acid-$^2$H$_3$ | 314.3 ± 0.5 |
| Docosanoic acid-$^2$H$_3$ | 343.3 ± 0.5 |
| Tetracosanoic acid-$^2$H$_3$ | 371.4 ± 0.5 |
| Hexadocosanoic acid-$^2$H$_3$ | 399.4 ± 0.5 |

Exemplary chromatograms for pristanic acid, phytanic acid, docosanoic acid, tetracosanoic acid, and hexadocosanoic acid obtained from analysis of standard samples are shown in FIGS. 1A, 2A, 3A, 4A, and 5A, respectively. Exemplary chromatograms for pristanic acid-$^2$H$_3$, phytanic acid-$^2$H$_3$, docosanoic acid-$^2$H$_3$, tetracosanoic acid-$^2$H$_3$, and hexadocosanoic acid-$^2$H$_3$ obtained from analysis of standard samples are shown in FIGS. 1B, 2B, 3B, 4B, and 5B, respectively.

Figure 6A:
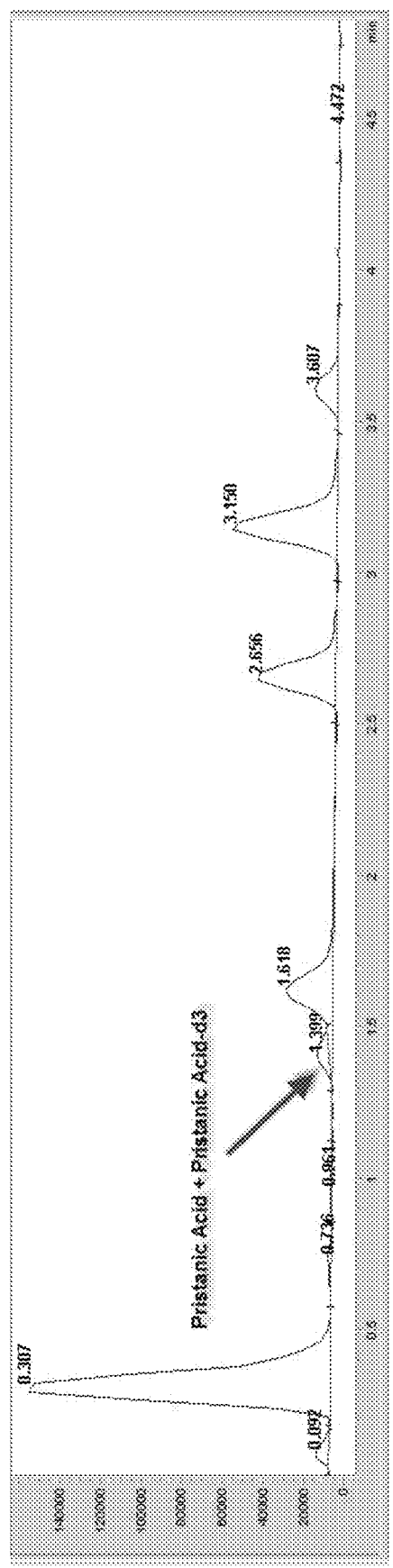
FIGS. 6A and 6B show an exemplary chromatogram (FIG. 6A) and spectrum (FIG. 6B) demonstrating detection of pristanic acid and pristanic acid-$^2H_3$ (internal standard) in a serum sample. Details are discussed in Example 4.
Figure 6B:
Figure 7A:
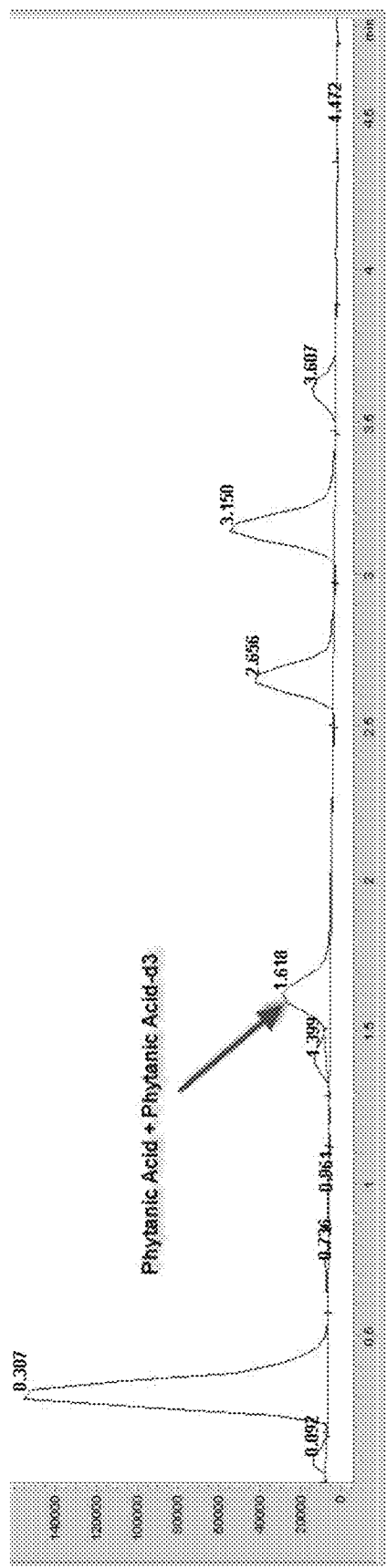
FIGS. 7A and 7B show an exemplary chromatogram (FIG. 7A) and spectrum (FIG. 7B) demonstrating detection of phytanic acid/phytanic acid-$^2H_3$ (internal standard) in a serum sample. Details are discussed in Example 4.
Figure 7B:
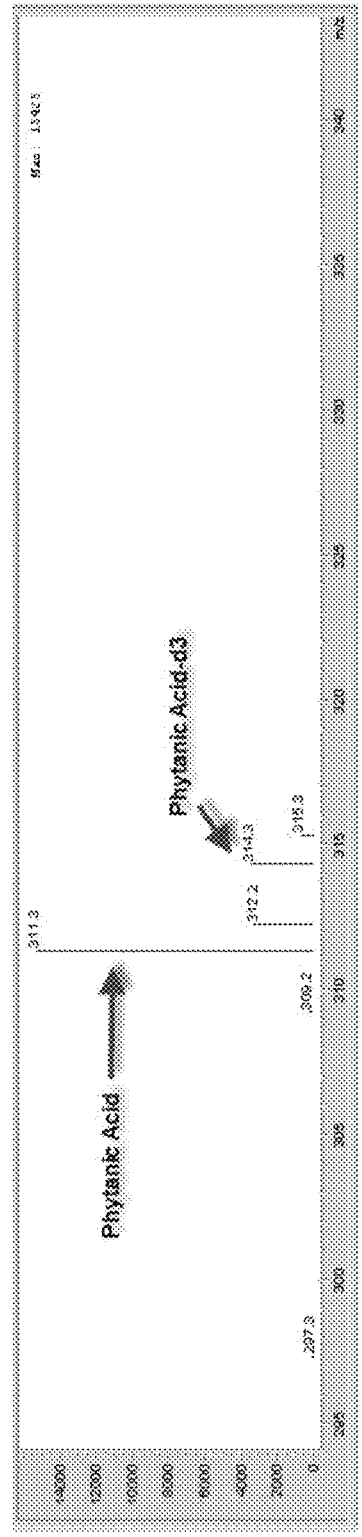
Figure 8A:
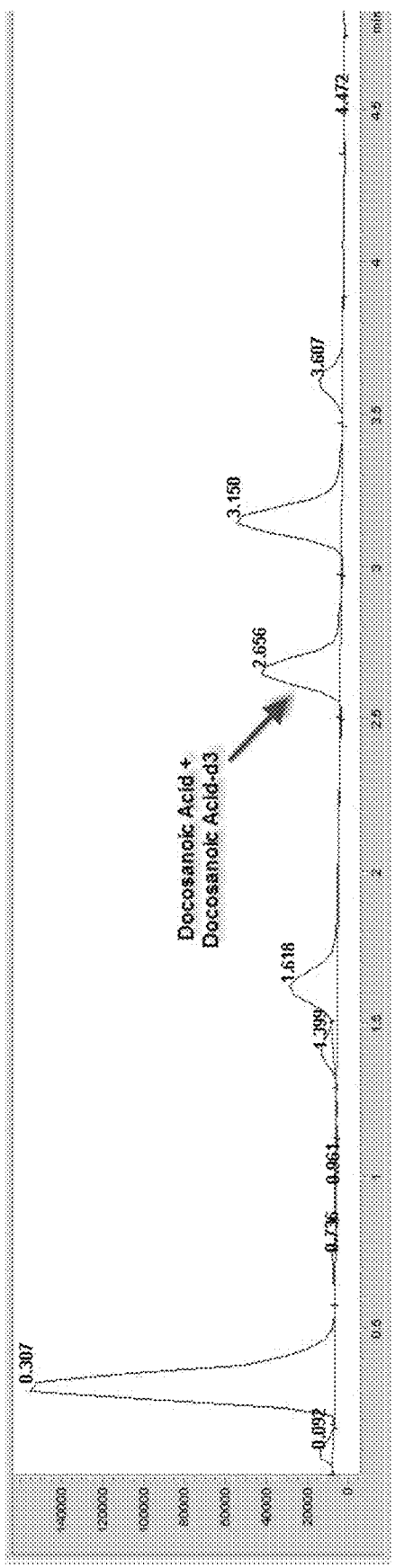
FIGS. 8A and 8B show an exemplary chromatogram (FIG. 8A) and spectrum (FIG. 8B) demonstrating detection of docosanoic acid/docosanoic acid-$^2H_3$ (internal standard) in a serum sample. Details are discussed in Example 4.
Figure 8B:
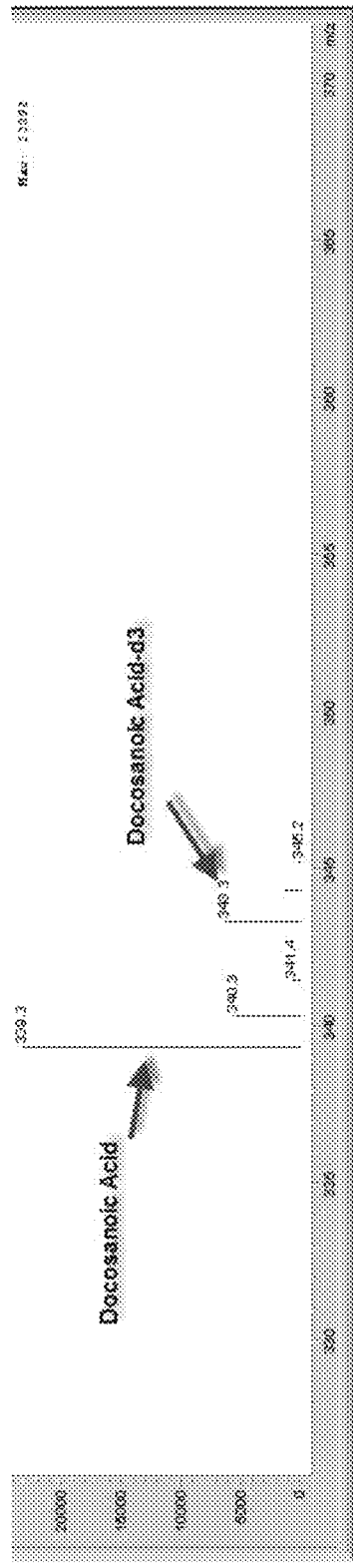
Figure 9A:
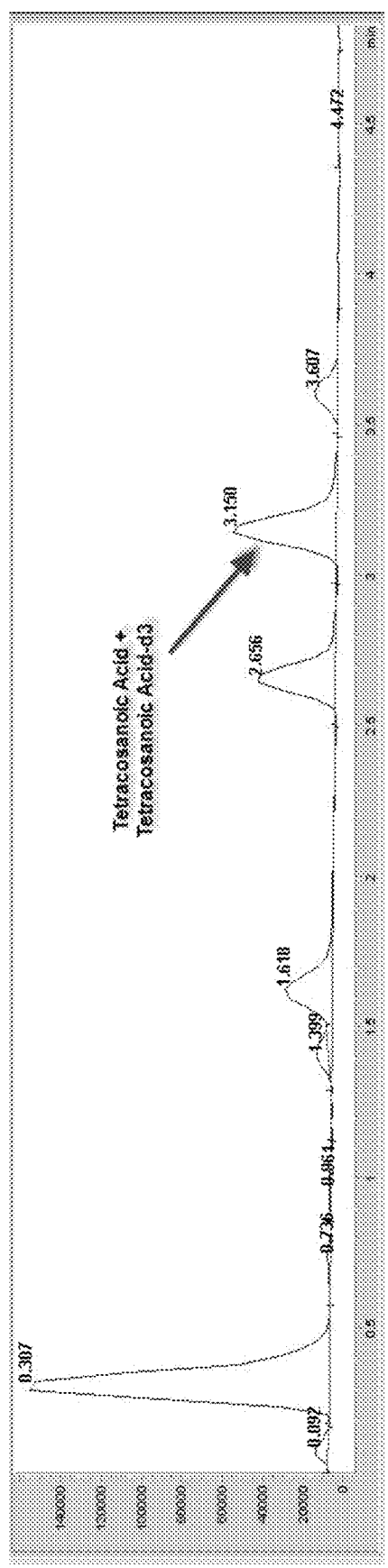
FIGS. 9A and 9B show an exemplary chromatogram (FIG. 9A) and spectra (FIG. 9B) demonstrating detection of tetracosanoic acid/tetracosanoic acid-$^2H_3$ (internal standard) in a serum sample. Details are discussed in Example 4.
Figure 9B:
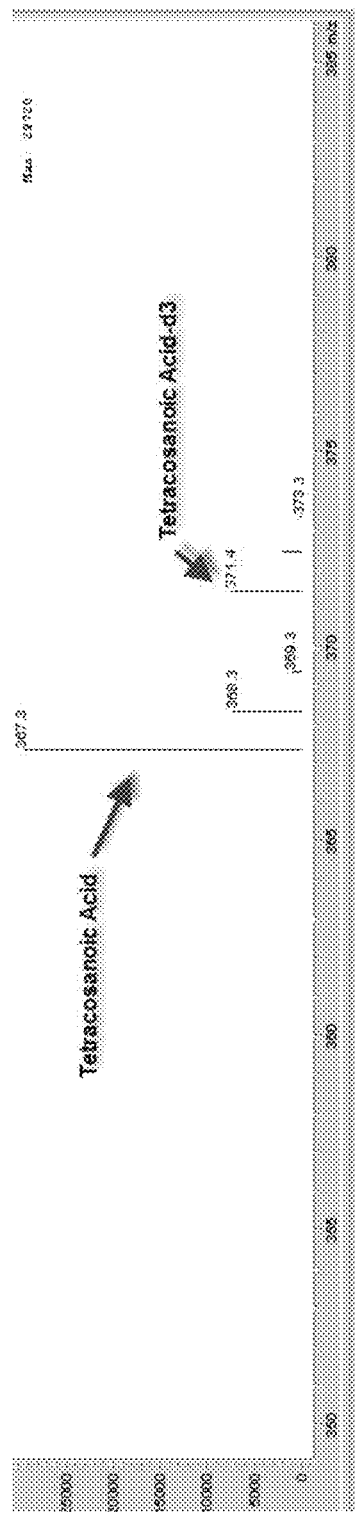
Figure 10A:
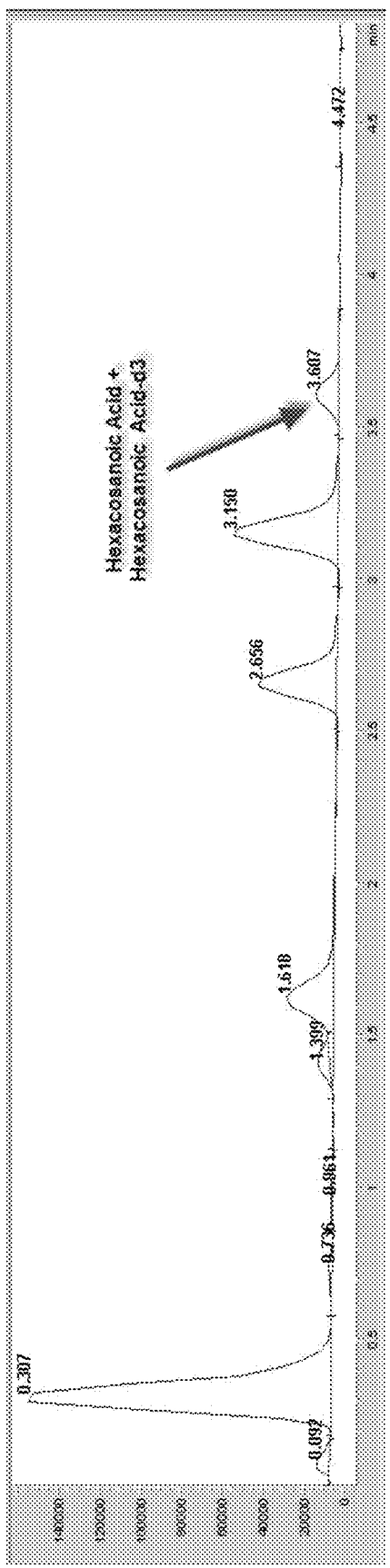
FIGS. 10A and 10B show an exemplary chromatogram (FIG. 10A) and spectrum (FIG. 10B) demonstrating detection of hexacosanoic acid/hexacosanoic acid-$^2H_3$ (internal standard) in a serum sample. Details are discussed in Example 4.
Figure 10B:
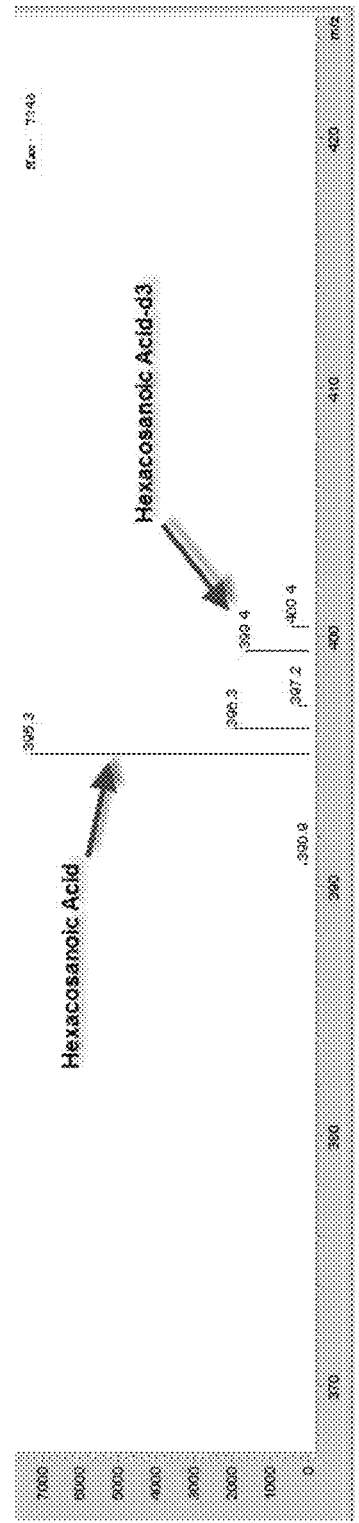

An exemplary chromatogram obtained from a serum sample is shown in FIGS. 6A, 7A, 8A, 9A, and 10A (each showing labeled peaks from pristanic acid, phytanic acid, docosanoic acid, tetracosanoic acid, and hexadocosanoic acid, respectively). Exemplary spectra obtained from mass spectrometric analysis a serum sample as described above are shown in FIGS. 6B (pristanic acid), 7B (phytanic acid), 8B (docosanoic acid), 9B (tetracosanoic acid), and 10B (hexadocosanoic acid). The spectra were collected by scanning Q1 across a m/z range of about 280-305 for pristanic acid, 295-341 for phytanic acid, 328-371 for docosanoic acid, 360-385 for tetracosanoic acid, and 369-422 for hexadocosanoic acid.

Example 5: Linearity of Detection for VLCFA and BCFA

Figure 11:
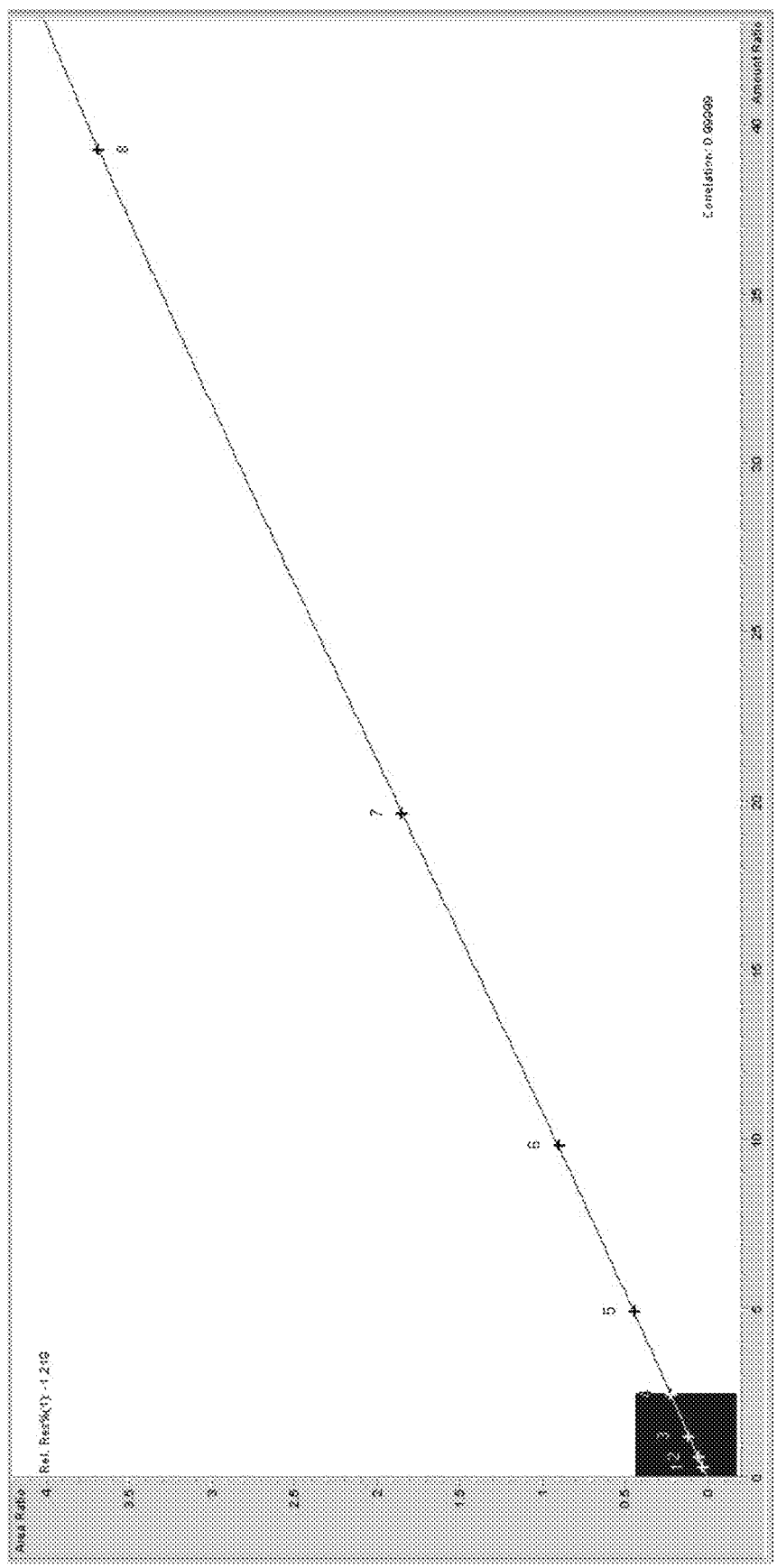
FIG. 11 shows an exemplary calibration curve generated for pristanic acid. Details are discussed in Example 4.
Figure 12:
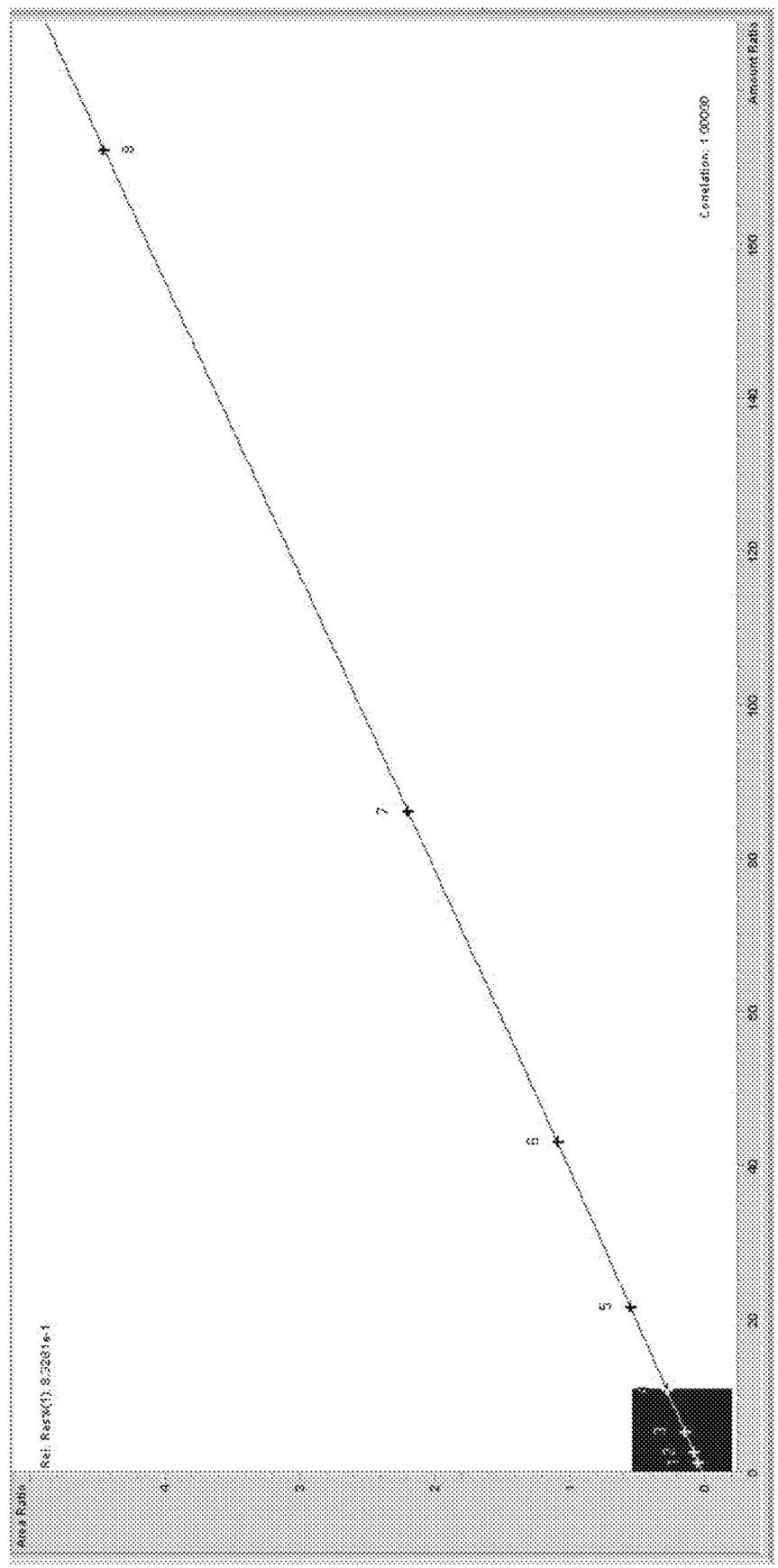
FIG. 12 shows an exemplary calibration curve generated for phytanic acid. Details are discussed in Example 4.
Figure 13:
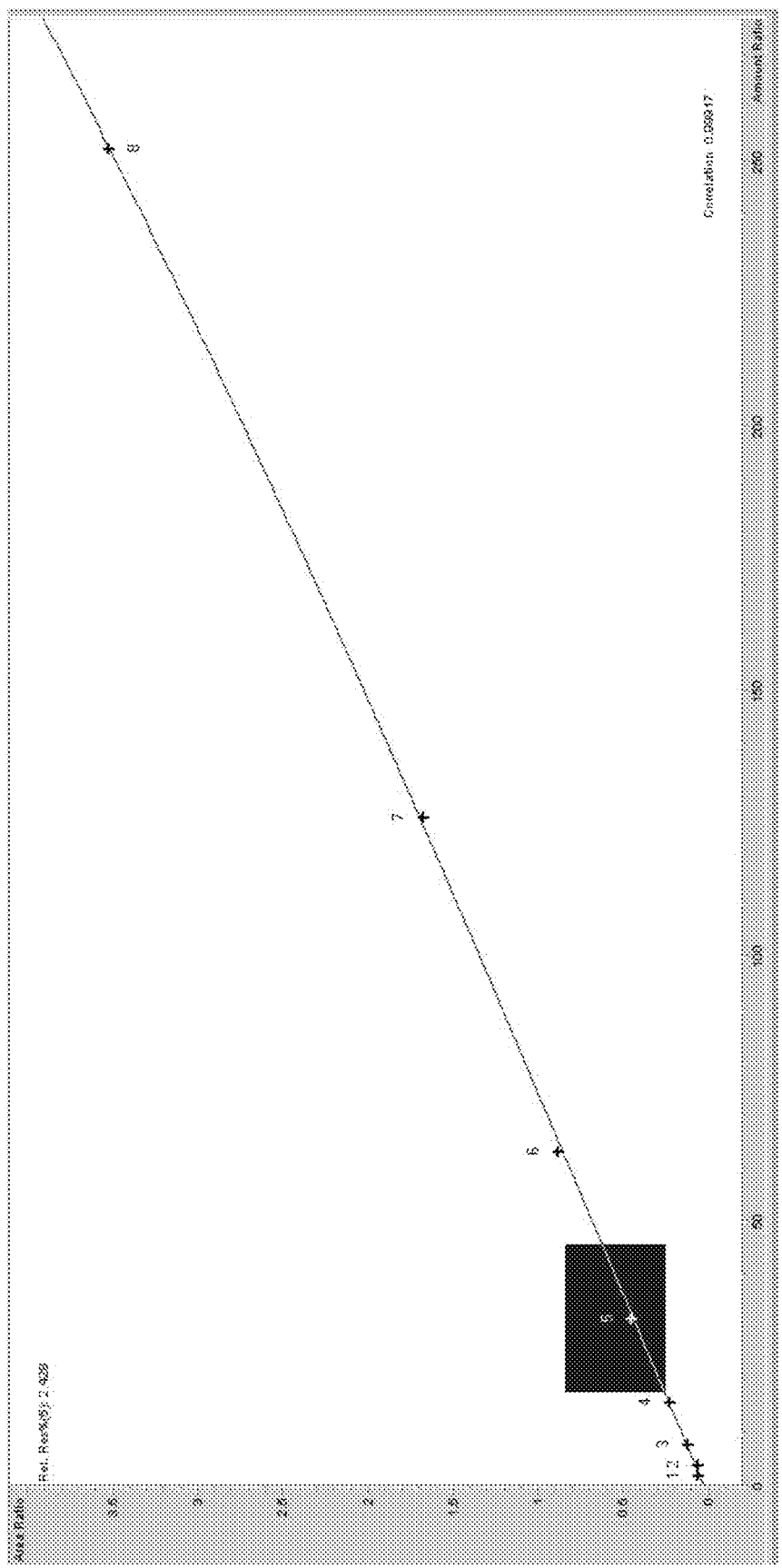
FIG. 13 shows an exemplary calibration curve generated for docosanoic acid. Details are discussed in Example 4.
Figure 14:
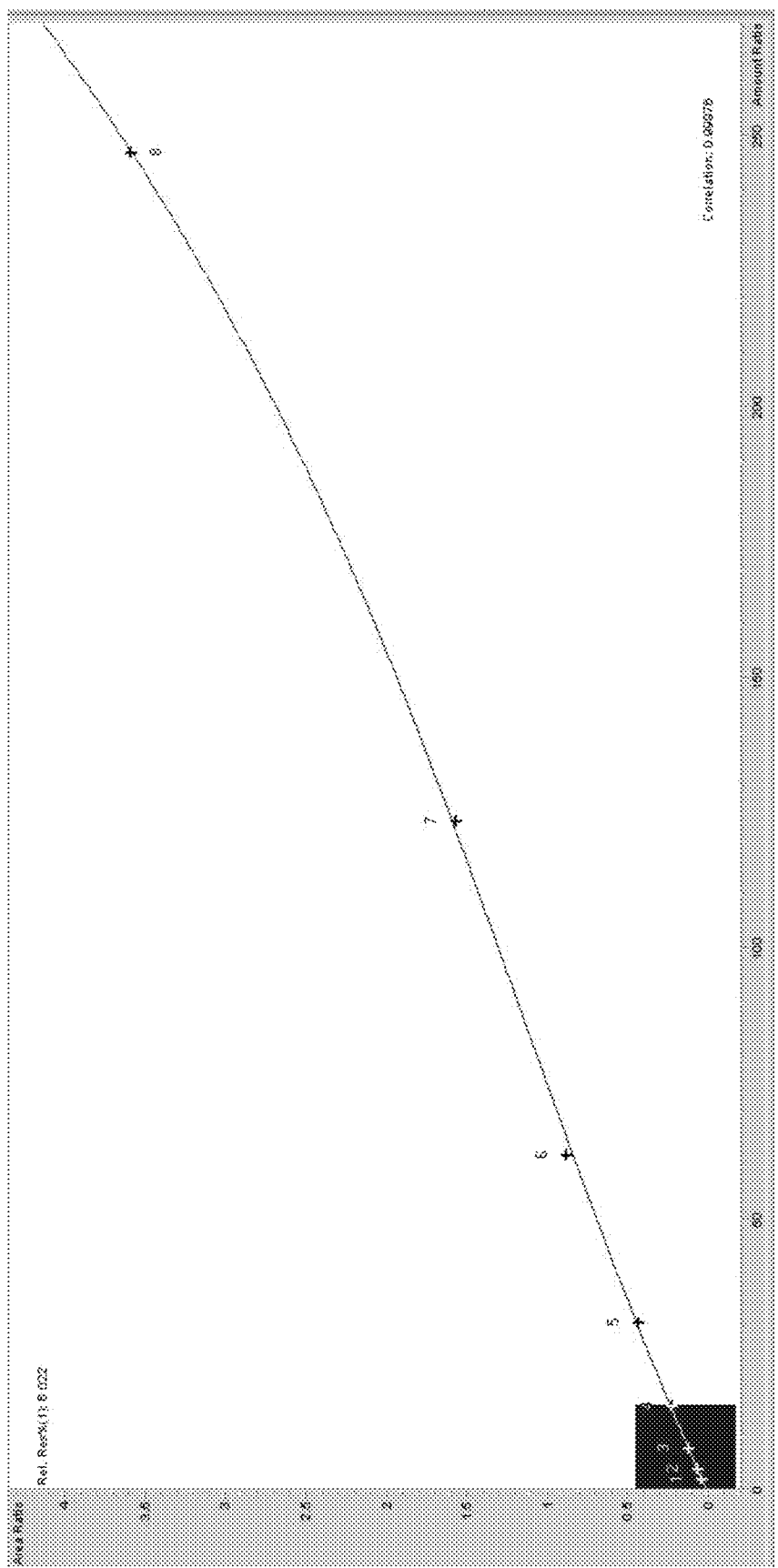
FIG. 14 shows an exemplary calibration curve generated for tetracosanoic acid. Details are discussed in Example 4.
Figure 15:
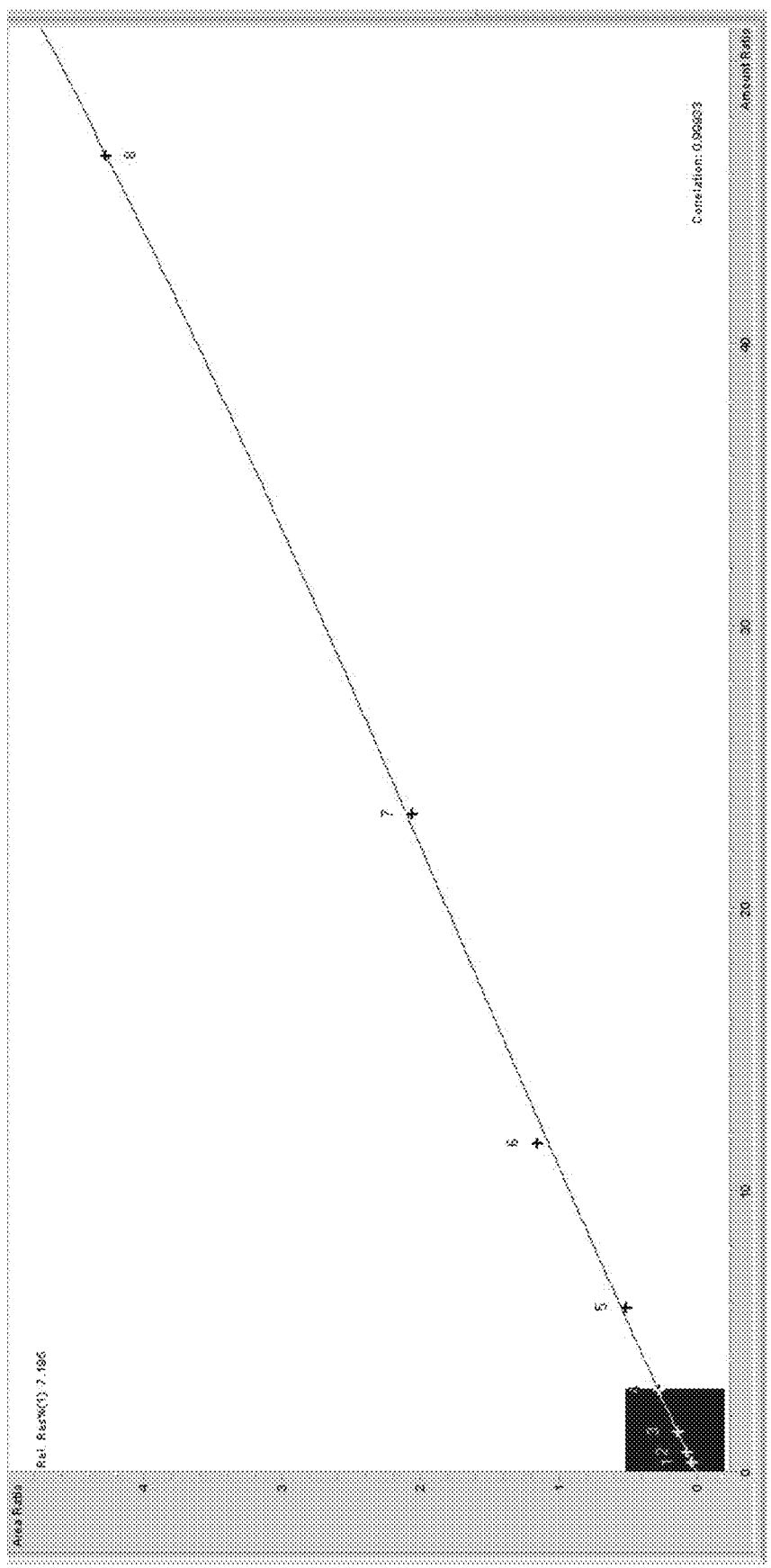
FIG. 15 shows an exemplary calibration curve generated for hexacosanoic acid. Details are discussed in Example 4.

Calibration curves were prepared for the quantitation of pristanic acid, phytanic acid, docosanoic acid, tetracosanoic acid, and hexadocosanoic acid in serum by analysis of standards across a range of concentrations. Exemplary calibration curves for the determination of pristanic acid and phytanic acid in serum specimens are shown in FIGS. 11-12, respectively. Exemplary calibration curves for the determination of docosanoic acid, tetracosanoic acid, and hexadocosanoic acid in serum specimens are shown in FIGS. 13-15, respectively. Analysis of the data generated for these standards demonstrates that the assay exhibits linear response for pristanic acid in the concentration range of about 0.15-60 µmol/L; for phytanic acid in the concentration range of about 0.24-200 µmol/L; for docosanoic acid in the concentration range of about 0.54-300 µmol/L; for tetracosanoic acid in the concentration range of about 0.36-300 µmol/L; for hexacosanoic acid in the concentration range of about 0.15-60 µmol/L.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining an amount of one or more underivatized fatty acids in a sample by mass spectrometry, the method comprising:
    (a) subjecting the sample containing an amount of one or more underivatized fatty acids to an ionization source to generate one or more underivatized fatty acid ions detectable by mass spectrometry, wherein the one or more underivatized fatty acids is selected from the group consisting of docosanoic acid, tetracosanoic acid, hexacosanoic acid, pristanic acid, and phytanic acid;
    (b) determining an amount of the one or more underivatized fatty acid ions by mass spectrometry; and
    (c) determining the amount of the one or more underivatized fatty acids in the sample from the amount of the one or more underivatized fatty acid ions determined in step (b).

2. The method of claim 1, wherein said fatty acid is pristanic acid.

3. The method of claim 1, wherein said fatty acid is phytanic acid.

4. The method of claim 1, wherein said fatty acid is docosanoic acid.

5. The method of claim 1, wherein said fatty acid is tetracosanoic acid.

6. The method of claim 1, wherein said fatty acid is hexacosanoic acid.

7. The method of claim 1, wherein the ionization source is electron ionization, chemical ionization, electrospray ionization (ESI), photon ionization, photoionization, atmospheric pressure photoionization (APPI), laser diode thermal desorption (LDTD), fast atom bombardment (FAB), liquid secondary ionization (LSI), matrix assisted laser desorption ionization (MALDI), field ionization, field desorption, thermospray ionization, plasmaspray ionization, surface enhanced laser desorption ionization (SELDI), inductively coupled plasma (ICP), or particle beam ionization.

8. The method of claim 1, wherein the sample is subjected to liquid/liquid extraction prior to ionization.

9. The method of claim 1, wherein the one or more fatty acids are subjected to a liquid chromatography column prior to ionization.

10. The method of claim 9, wherein the liquid chromatography column comprises a high performance liquid chromatography (HPLC), reverse phase liquid chromatography (RPLC), turbulent flow liquid chromatography (TFLC), or high turbulence liquid chromatography (HTLC).

11. The method of claim 1, wherein the method further comprises determining an amount of one or more internal standards added prior to step (a).

12. The method of claim 11, wherein the internal standard is pristanic acid-$^2H_3$ phytanic acid-$^2H_3$, docosanoic acid-$^2H_3$, tetracosanoic acid-$^2H_3$, or hexacosanoic acid-$^2H_3$.

13. A method of diagnosing or monitoring a peroxisomal disorder comprising determining an amount of one or more fatty acids in a patient sample by steps of claim 1.

14. The method of claim 13, wherein an abnormal level of fatty acids is indicative of the peroxisomal disorder.

15. The method of claim 14, wherein the peroxisomal disorder is Zellweger syndrome, pseudo-Zellweger syndrome, infantile and adult Refsum disease, adrenoleukodystrophy, rhizomelic chondrodysplasia *punctata* type 1 (RCDP-1), D-bifunctional protein deficiency, or acyl-coA oxidase deficiency.

16. A method for determining an amount of one or more underivatized fatty acids in a sample by mass spectrometry, the method comprising:
   (a) subjecting the sample containing an amount of underivatized fatty acids to a hexane extraction, wherein the one or more underivatized fatty acids is selected from the group consisting of docosanoic acid, tetracosanoic acid, hexacosanoic acid, pristanic acid, and phytanic acid;
   (b) subjecting the sample to liquid chromatography;
   (c) subjecting the sample to an ionization source to generate one or more underivatized fatty acid ions detectable by mass spectrometry;
   (d) determining an amount of the one or more underivatized fatty acid ions by mass spectrometry; and
   (e) determining the amount of the underivatized fatty acids in the sample from the amount of the one or more underivatized fatty acid ions determined in step (d).

17. The method of claim 16, wherein said fatty acid is pristanic acid.

18. The method of claim 16, wherein said fatty acid is phytanic acid.

19. The method of claim 16, wherein said fatty acid is docosanoic acid.

20. The method of claim 16, wherein said fatty acid is tetracosanoic acid.

21. The method of claim 16, wherein said fatty acid is hexacosanoic acid.

22. The method of claim 16, wherein the ionization source is electron ionization, chemical ionization, electrospray ionization (ESI), photon ionization, photoionization, atmospheric pressure photoionization (APPI), laser diode thermal desorption (LDTD), fast atom bombardment (FAB), liquid secondary ionization (LSI), matrix assisted laser desorption ionization (MALDI), field ionization, field desorption, thermospray ionization, plasmaspray ionization, surface enhanced laser desorption ionization (SELDI), inductively coupled plasma (ICP), or particle beam ionization.

23. The method of claim 16, wherein said sample is subjected to an acid hydrolysis prior to ionization.

24. The method of claim 16, wherein the method further comprises determining an amount of one or more internal standards added prior to step (a).

25. The method of claim 24, wherein the internal standard is pristanic acid-$^2H_3$ phytanic acid-$^2H_3$, docosanoic acid-$^2H_3$, tetracosanoic acid-$^2H_3$, or hexacosanoic acid-$^2H_3$.

26. A method of diagnosing or monitoring a peroxisomal disorder comprising determining an amount of one or more fatty acids in a patient sample by steps of claim 16.

27. The method of claim 26, wherein an abnormal level of fatty acids is indicative of the peroxisomal disorder.

28. The method of claim 27, wherein the peroxisomal disorder is Zellweger syndrome, pseudo-Zellweger syndrome, infantile and adult Refsum disease, adrenoleukodystrophy, rhizomelic chondrodysplasia *punctata* type 1 (RCDP-1), D-bifunctional protein deficiency, or acyl-coA oxidase deficiency.

* * * * *